(12) United States Patent
Peters et al.

(10) Patent No.: US 7,740,575 B2
(45) Date of Patent: *Jun. 22, 2010

(54) FLUID PRESSURE GENERATING MEANS

(75) Inventors: William Suttle Peters, Auckland (NZ); Hans Hansforth Henrichsen, Wollongong (AU); Peter Andrew Watterson, Denistone (AU)

(73) Assignee: Sunshine Heart, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/768,130

(22) Filed: Jun. 25, 2007

(65) Prior Publication Data

US 2008/0255405 A1 Oct. 16, 2008

Related U.S. Application Data

(63) Continuation of application No. 10/380,789, filed on Oct. 2, 2003, now Pat. No. 7,306,558.

(30) Foreign Application Priority Data

Jul. 30, 2001 (AU) .................................. PR6690
Jul. 22, 2002 (WO) ..................... PCT/AU02/00974

(51) Int. Cl.
*A61N 1/362* (2006.01)
(52) U.S. Cl. .............................. 600/16; 600/18; 623/3.1
(58) Field of Classification Search .................. 600/16, 600/18; 623/3.1
See application file for complete search history.

(56) References Cited

U.S. PATENT DOCUMENTS

| 4,014,318 A | 3/1977 | Dockum et al. |
| 4,176,411 A | 12/1979 | Runge |
| 4,195,623 A | 4/1980 | Zeff et al. |
| 4,277,706 A * | 7/1981 | Isaacson ...................... 310/80 |
| 4,304,225 A | 12/1981 | Freeman |
| 4,583,523 A | 4/1986 | Kleinke et al. |
| 4,630,597 A | 12/1986 | Kantrowitz et al. |
| 4,771,765 A | 9/1988 | Choy et al. |
| 4,809,676 A | 3/1989 | Freeman |

(Continued)

FOREIGN PATENT DOCUMENTS

EP 0 216 042 A1 4/1987

(Continued)

*Primary Examiner*—George R Evanisko
*Assistant Examiner*—Joseph Stoklosa
(74) *Attorney, Agent, or Firm*—Faegre & Benson LLP

(57) ABSTRACT

A fluid pressure generating means (10) for a heart assist device having blood pumping means. The pressure generating means (10) includes a housing (11), defining an interior volume (18), and having a substantially rigid first housing portion (12), a substantially rigid second housing portion (14), a flexible third housing portion (16) extending between the first (12) and second (14) housing portions and an inlet/outlet port (15) adapted for fluid communication with the blood pumping means. The pressure generating means (10) also includes a fluid filling the housing and a motor (20) disposed within the housing (11) and connected between the first (12) and second (14) housing portions. Actuation of the motor (20) moves the first (12) and second (14) housing portions relative to one another to generate fluid pressure changes at the inlet/outlet port (15). A related heart assist device and method for the treatment of congestive heart failure, myocardial ischemia and like conditions are also disclosed.

19 Claims, 7 Drawing Sheets

U.S. PATENT DOCUMENTS

| | | | |
|---|---|---|---|
| 4,813,952 A | | 3/1989 | Khalafalla |
| 4,979,936 A | | 12/1990 | Stephenson et al. |
| 5,205,810 A | | 4/1993 | Guiraudon et al. |
| 5,222,980 A | | 6/1993 | Gealow |
| 5,267,940 A | | 12/1993 | Moulder |
| 5,273,518 A | | 12/1993 | Lee |
| 5,360,445 A | * | 11/1994 | Goldowsky ............... 623/3.22 |
| 5,372,573 A | | 12/1994 | Habib |
| 5,429,584 A | | 7/1995 | Chiu |
| 5,647,380 A | | 7/1997 | Campbell et al. |
| 5,980,448 A | | 11/1999 | Heilman et al. |
| 6,030,336 A | * | 2/2000 | Franchi ..................... 600/18 |
| 6,045,496 A | | 4/2000 | Pacella et al. |
| 6,471,633 B1 | | 10/2002 | Freed |
| 6,808,484 B1 | | 10/2004 | Peters et al. |
| 7,306,558 B2 | * | 12/2007 | Peters et al. ............... 600/16 |

FOREIGN PATENT DOCUMENTS

| | | |
|---|---|---|
| EP | 0 216 042 B1 | 4/1987 |
| FR | 2 458 288 | 1/1981 |
| FR | 2 767 874 | 3/1999 |
| JP | 10328297 | 12/1998 |
| JP | H11-285529 | 10/1999 |
| WO | WO 92/08500 | 5/1992 |
| WO | WO 98/05289 | 2/1998 |
| WO | WO 99/04833 | 2/1999 |
| WO | WO 00/76288 | 12/2000 |
| WO | WO 01/13974 | 3/2001 |

* cited by examiner

FLUID PRESSURE GENERATING MEANS

RELATED INFORMATION

This application is a continuation of application Ser. No. 10/380,789 filed on Oct. 2, 2003, now U.S. Pat. No. 7,306,558 and which claims priority to Australian Provisional Application No. PR 6690, filed Jul. 30, 2001, and to PCT Application PCT/AU02/00974, filed Jul. 22, 2002 (International Publication No. WO 03/011365).

FIELD OF THE INVENTION

The present invention relates to a fluid pressure generating means for use with a heart assist device.

BACKGROUND OF THE INVENTION

The applicant's international PCT patent application no. PCT/AU00/00654 (International publication no. WO 00/76288) entitled "Heart Assist Devices, Systems and Methods" ("the PCT application") discloses numerous embodiments of a novel heart assist device adapted for implantation into a patient. Broadly speaking, the disclosed heart assist devices include: an aortic compression means adapted, when actuated, to compress an aorta of a patient; a fluid reservoir; and a fluid pressure generating means adapted to pump fluid from the fluid reservoir to the aortic compression means so as to actuate the aortic compression means in counterpulsation with the patient's heart. The relevant portions of the PCT application are incorporated herein by cross-reference.

It is a first object of the present invention to provide improved fluid pressure generating means suitable for use with the aortic compression means described in the PCT application. It is a second object to provide a fluid pressure generating means which may be placed more conveniently into the body of a patient.

SUMMARY OF THE INVENTION

Accordingly, in a first aspect, the present invention provides a fluid pressure generating means for a heart assist device having blood pumping means, the pressure generating means including:

a housing, defining an interior volume, and having a substantially rigid first housing portion, a substantially rigid second housing portion, a flexible third housing portion extending between the first and second housing portions and an inlet/outlet port adapted for fluid communication between the interior volume and the blood pumping means;

a fluid filling the housing; and a motor or other actuator means disposed within the interior volume of the housing and connected between the first and second housing portions, wherein actuation of the motor or other actuator means moves the first and second housing portions relative to one another to generate fluid pressure changes at the inlet/outlet port.

In one preferred form, the third housing portion has an outer edge about its periphery and inner edge about an opening and is joined along the outer and the inner edge to the first and second housing portions respectively.

In another preferred form, the third housing portion is connected to only one of the first and second housing portions and abuts against the other of the first and second housing portions.

The blood pumping means is preferably adapted to displace blood in the aorta, more specifically the ascending aorta, and preferably by compressing or deforming the aorta of a patient in counter-pulsation with the patient's heart. More preferably, the blood pumping means is adapted to displace blood from the ascending aorta of the patient. In an alternative arrangement, the fluid pressure generating means can be used to drive a conventional left ventricular assist device or an extra-ventricular co-pulsation heart compression device. In such an arrangement suitable valves are used to ensure the correct direction of blood flow through a pumping chamber driven by the fluid pressure generating means.

In a further preferred form, one of the first and second housing portions is moveable and the other of the first and second housing portions is fixed, the moveable housing portion being exposed to the outside of the heart assist device and adapted to interface with the lung of a patient.

In a yet further preferred form, one of the first and second housing portions is moveable and the other of the first and second housing portions is fixed, the moveable housing portion not being exposed to the outside of the heart assist device and the device including a flexible compliance chamber. The compliance chamber is desirably in contact with the lung of a patient.

The actuating means desirably includes a nut coupled to one of the first and second housing portions and a threaded shaft coupled to the other of the first and second housing portions, the threaded shaft and the nut being threadedly engaged and the motor being adapted to rotate the nut relative to the threaded shaft. In one arrangement, the nut is connected to the moveable one of the first and second housing portions and the threaded shaft is connected to the fixed one of the first and second housing portions. In another arrangement, the threaded shaft is connected to the moveable one of the first and second housing portions and the nut is connected to the fixed one of the first and second housing portions.

In an embodiment, the outflow of the fluid from the inlet/outlet port is axial to the housing. In another embodiment, the outflow of the fluid from the inlet/outlet port is radial to the housing. In a further embodiment, the outflow of the fluid from the inlet/outlet port is tangential to the housing.

A surface of the device is preferably curved to fit snugly with the chest wall and/or mediastinum and/or diaphragm of a patient.

The blood pumping means is preferably in the form of a fluid operated cuff adapted to surround the patient's aorta.

The fluid filling the housing is preferably a liquid. The liquid is preferably an oil or saline. The oil is preferably a silicone oil and desirably has viscosity between 10 and 100 centistokes, most desirably between 10 and 30 centistokes.

In a second aspect, the present invention provides a heart assist device including:

a blood pumping means adapted, when actuated, to cause or assist the movement of blood around the patient's vasculature;

a fluid reservoir;

a fluid pressure generating means adapted to pump fluid from the fluid reservoir to the blood pumping means; and a housing containing both the fluid reservoir and the fluid pressure generating means that is so shaped and dimensioned as to be adapted to lie in the plueral cavity, adjacent to the lung, when the blood pumping means is functionally positioned within the patient.

In a third aspect, the present invention provides a method for the treatment of congestive heart failure, myocardial ischemia and like conditions, the method comprising:

inserting into the pleural cavity within the chest (preferably the right chest) of a patient, and adjacent to the lung, a housing containing a fluid reservoir and a fluid pressure generating means adapted to pump fluid from the fluid reservoir to blood pumping means functionally placed in the patient so as to cause or assist the movement of blood around the patient's vasculature.

Until now most implanted heart assist devices have been placed in the abdominal cavity of a patient. This is disadvantageous as it complicates the surgical procedure and is unduly invasive for the patient. The few proposals for placement of such a device in the chest cavity have proposed the placement of the device against the inside of the chest wall so that the device can be wired to the ribs of the patient. It was apparently felt that this was necessary to support the weight of the device and to prevent it from moving around in the patient. The present inventors have found that the device may be placed against the mediastinum directly adjacent the patient's heart and attached to surrounding soft tissue. The device will thus lie in the plueral cavity, adjacent to the lung. The device preferably lies in a sagittal plane within the patient's body. Desirably, the device will not touch the inside surface of the chest wall at all. This placement will reduce pain for the patient and make placement of the device easier for the surgeon implanting the device.

Preferably, the blood pumping means referred to in the above method is adapted to compress the aorta of a patient in counter-pulsation with the patient's heart. More preferably, the blood pumping means is adapted to compress the ascending aorta of the patient.

In a fourth aspect, the present invention provides a heart assist device including:

a blood pumping means adapted, when actuated, to cause or assist the movement of blood around the patient's vasculature;

a fluid reservoir; and a fluid pressure generating means driven by an electric motor and adapted to pump a liquid from the fluid reservoir to the blood pumping means;

the electric motor having a cogging torque which is sufficiently low that the natural systolic blood pressure of the patient is sufficient to cause liquid in the blood pumping means to be returned to the fluid reservoir in the event that the electric motor stops.

BRIEF DESCRIPTION OF THE DRAWINGS

Preferred embodiments of the invention will now be described, by way of examples only, with reference to the accompanying drawings in which:

FIG. 4b is an underside perspective view of a housing portion of the fluid pressure generating means shown in FIG. 4a;

FIG. 4c is a schematic longitudinal sectional view of the fluid pressure generating means shown in FIG. 4a.

DETAILED DESCRIPTION OF THE PREFERRED EMBODIMENTS

Figure 1:
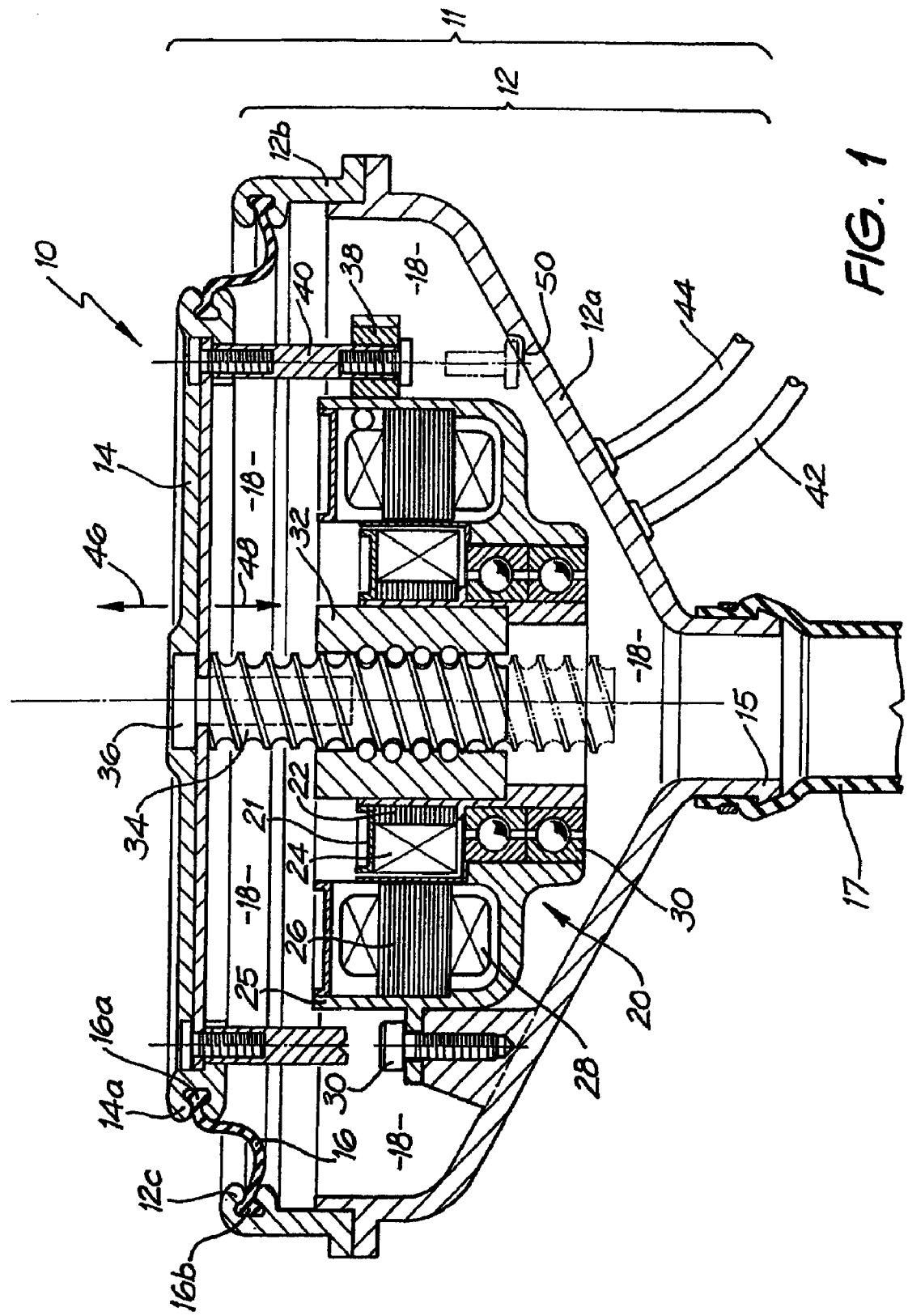
FIG. 1 is a schematic longitudinal sectional view of a first embodiment of a fluid pressure generating means according to the invention.

Referring firstly to FIG. 1, there is shown a schematic longitudinal sectional view of a first embodiment of a fluid pressure generating means according to the invention, in the form of pump 10. The pump 10 includes a housing, indicated generally by the reference numeral 11, comprising a substantially rigid bell-shaped first housing portion 12, a substantially rigid flat circular second housing portion 14 and a flexible third housing portion or membrane 16.

The first, second and third housing portions 12, 14 and 16 together define an external boundary of the housing 11 around an interior volume denoted 18, which is filled with a silicone oil. The second housing portion 12 is itself formed from a cone-shaped portion 12a which is sealingly connected, after assembly of the pump 10, to a cylindrical portion 12b.

The cone-shaped portion 12a also includes an inlet/outlet port 15, which is connected in fluid communication with an aortic compression means or blood pumping means (not shown) by a conduit 17.

The membrane 16 is substantially annular in configuration and has enlarged inner and outer edges 16a and 16b which are sealingly received in corresponding circumferential recesses 12c and 14a provided in the first and second housing portions 12 and 14 respectively.

The pump 10 also includes an electric motor, indicated generally by the reference numeral 20, within the interior volume 18 of the housing 11. The motor includes a rotor 21, rotor laminations 22, magnets 24, stator 25, stator laminations 26, end windings 28 and bearings 30.

The stator 25 is fixed to the housing portion 12a by a number of screws 30 (only one shown). The rotor 21 is fixed to a nut 32, which is itself threadedly engaged with a threaded shaft 34 through ball bearings (not shown). The shaft 34 is fixed to the housing portion 14 by screw 36. The stator 25 also includes a number of guide journals 38 (only one shown) through which are guided a corresponding number of shafts 40 that depend from the housing portion 14.

Power and control signals are fed to the motor 20 through lines 42 and 44 respectively.

The operation of the pump 10 will now be described. Energising the motor 20 to rotate in a first direction rotates the nut 32 relative to the threaded shaft 34 which causes the threaded shaft 34 to move in a direction parallel to its longitudinal axis in a first direction indicated by arrow 46. FIG. 1 shows the shaft 34 at the end of its travel in this direction and after driving the housing portion 14 away from the housing portion 12 to increase the interior volume 18 and cause a suction or negative pressure at the inlet/outlet port 15. This suction actively deflates the aortic compression means (not shown).

Energising the motor to rotate in the opposite direction causes the threaded shaft 34 to move parallel to the longitudinal axis in the opposite direction indicated by arrow 48 and draw the portion 14 towards the housing portion 12. The end limit of travel in this direction is indicated in phantom in FIG. 1 and, with reference to which it should be noted that, the guide shaft 40 abuts the inner surface of the housing portion 12a at the limit of its travel at recess 50. Drawing the flexible portion 14 towards the housing portion 12 reduces the interior volume 18 which causes a positive pressure at the inlet/outlet port 15 and drives fluid from the interior volume 18 to inflate the aortic compression means.

The motor 20 is actuated cyclically in this manner in counterpulsation with the patient's heart in response to signals received from an ECG monitor or systemic arterial pressure, as disclosed in the PCT application.

Figure 2:
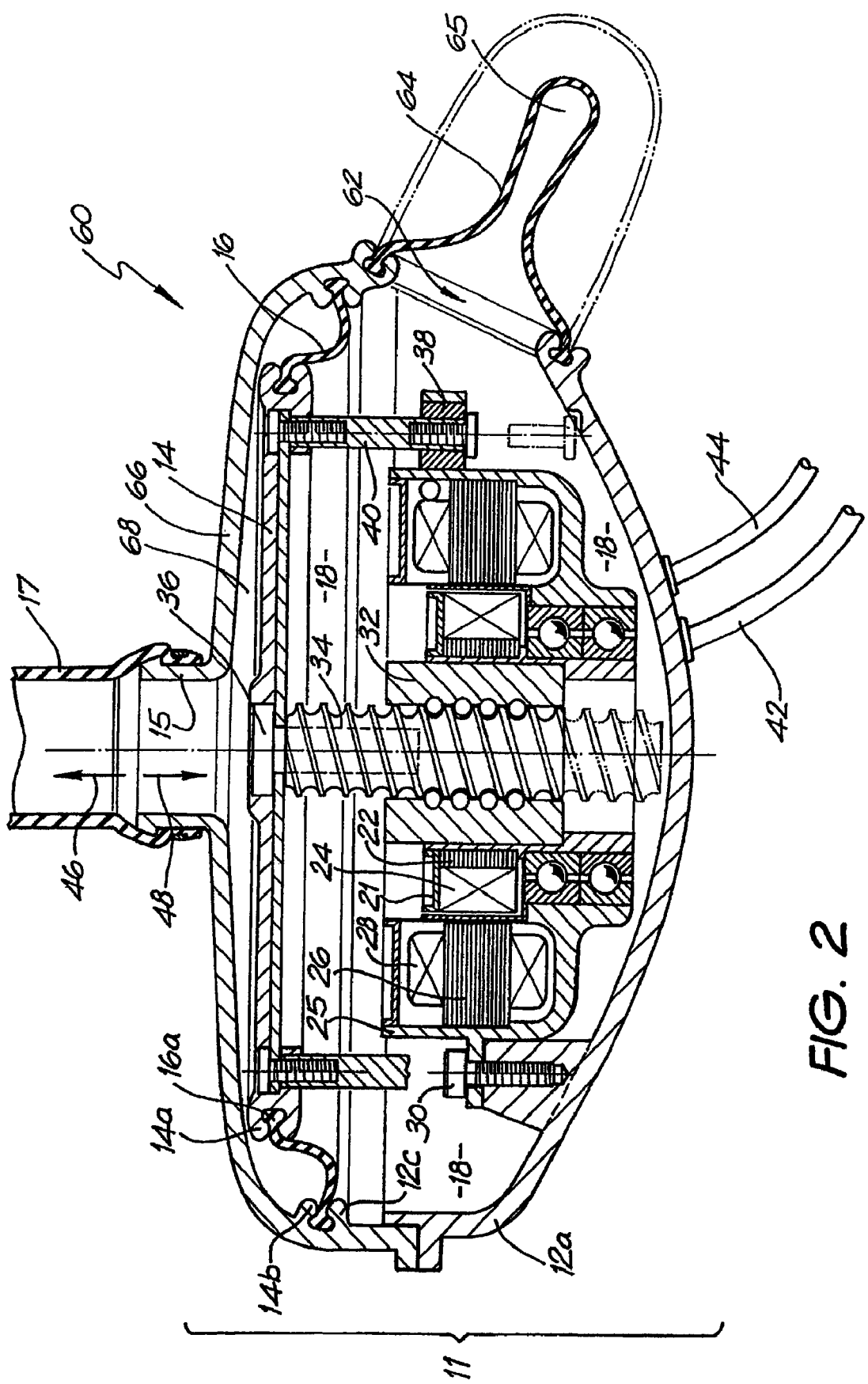
FIG. 2 is a schematic longitudinal sectional view of a second embodiment of a fluid pressure generating means according to the invention.

Referring now to FIG. 2, there is shown a schematic longitudinal sectional view of a second embodiment of a fluid pressure generating means according to the invention, in the form of pump 60. The pump 60 is similar to the pump 10 shown in FIG. 1 and like features are indicated with like reference numerals. Differences between the pumps 10 and 60 are described in detail below.

Firstly, the housing portion 12a of the pump 60 includes an opening 62 sealed by a second flexible membrane 64 which forms a compliance chamber 65. The chamber 65 is in fluid communication with the interior volume 18. Secondly, the inlet/outlet port 15 is provided in a further housing portion 66 which is sealed with respect to the side of the second housing portions 14 and third housing portion 16 that is remote the motor 20. The housing portion 66 creates, in conjunction with the housing portions 14 and 16, a second interior volume 68 in fluid communication with the aortic compression means or blood pumping means (not shown) via conduit 17.

The operation of the pump 60 is similar to that as described with reference to the pump 10 with the exception that the movement of the housing portion 14 causes volume changes in the second interior volume 68 which in turn inflates and deflates the aortic compression means. The movement of the housing portion 14 also causes fluid movement in the part of the interior volume 18 within the first, second and third housing portions 12, 14 and 16 and these changes cause an identical volume change in the interior of the compliance chamber 65, which is shown having a decreased volume in response to the compression means being inflated. The chamber 65 will have an increased volume in response to the compression means being deflated, as is shown in phantom.

As the interior volumes 18 and 68 are maintained sealed from one another by the second and third housing portions 14 and 16, the pump 60 can be configured to use different fluids in each of the interior volumes 18 and 60, as desired. For example, a saline solution can be used in the interior volume 68 and a lubricating oil can be used in the interior volume 18 which contains the motor 20.

Figure 3:
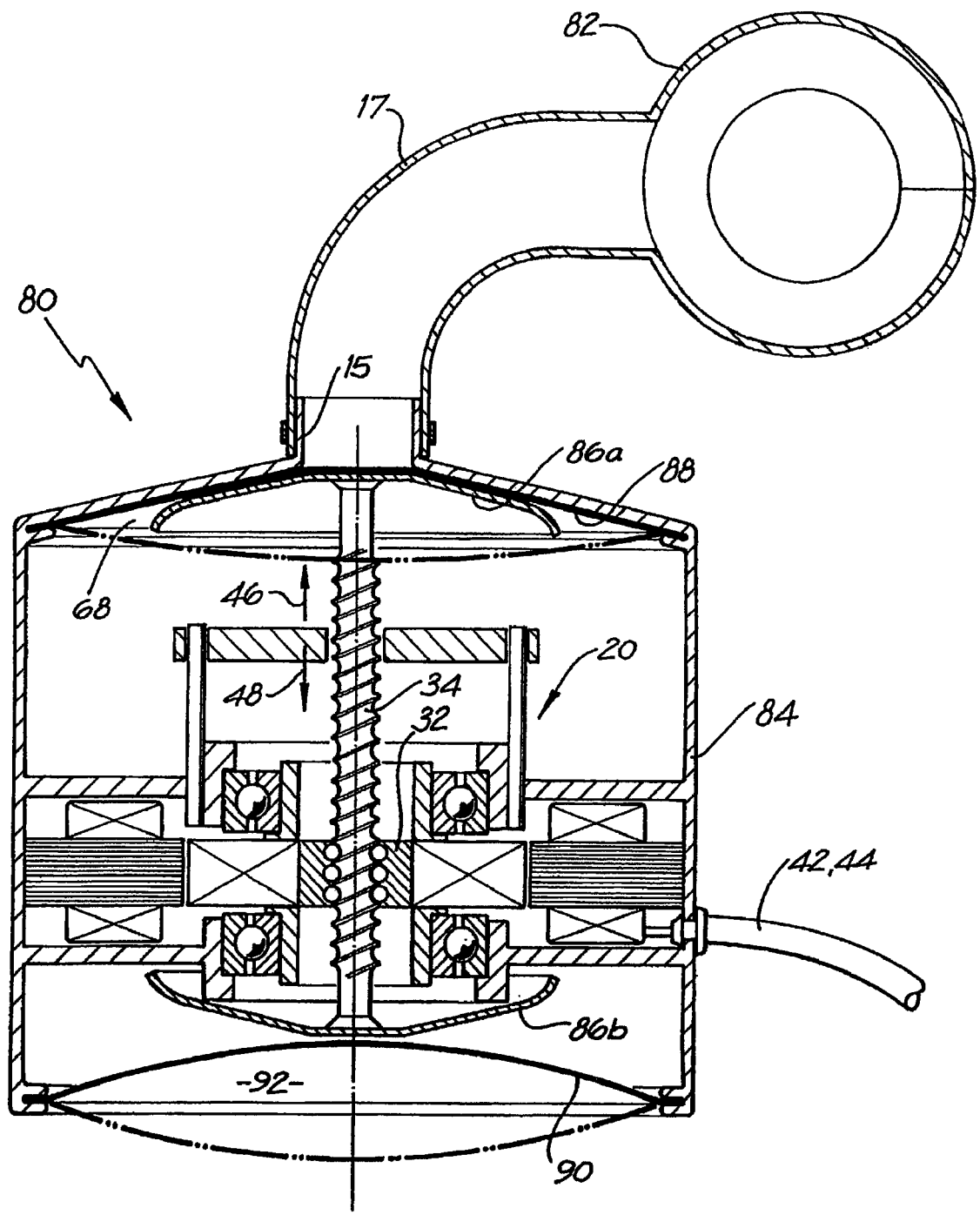
FIG. 3 is a schematic longitudinal sectional view of a third embodiment of a fluid pressure generating means according to the invention connected to a heart assist device.

FIG. 3 is a schematic cross sectional side view of a third embodiment of a fluid pressure generating means according to the invention, in the form of pump 80. The pump 80 is shown connected to an aortic compression means or blood pumping means in the form of cuff 82. The pump 80 is similar to the pump 60 described in relation to FIG. 2 and like reference numerals will be used to indicate like features. Differences between the pumps 60 and 80 are described in detail below.

Firstly, the pump 80 has a first external substantially rigid cylindrical housing portion 84, a pair of second internal substantially rigid housing portions 86a and 86b and a third substantially flexible housing portion 88. The latter seals an end of the first housing portion 84. The pump 80 also includes a second flexible housing portion 90 which seals the other end of the second housing portion 84 and forms a compliance chamber 92. Secondly, the second housing portion 86 and the third flexible housing portion 88 abut, but are not connected, to each other.

The operation of the pump 80 is similar to that described with reference to pump 60 in that the motor 20 is energized to reciprocally drive the threaded shaft 34 and thus the second housing portion 86a in directions 46 and 48 parallel to the longitudinal axis of the threaded shaft 34.

FIG. 3 shows the pump 80 in a position after movement of the second housing portion 86a in the direction 46 and driving fluid from the second interior volume 68 into the cuff 82 to inflate same. In this position, the second membrane of 64 is drawn into the interior of the second housing portion 84 to maintain the interior volume 18 constant. Driving the threaded shaft 34 in the opposite direction 48 results in the housing portion 86b forcing the membrane 64 to the position shown in phantom which is external the second housing portion 84. This also results in the third housing portion 88 being drawn to the position also shown in phantom to maintain the interior volume 18 constant. As previously described in relation to pump 60, when the third housing portion 86 is in this position fluid is drawn into the second interior volume 68 from the cuff 82 to deflate same.

Figure 4A:
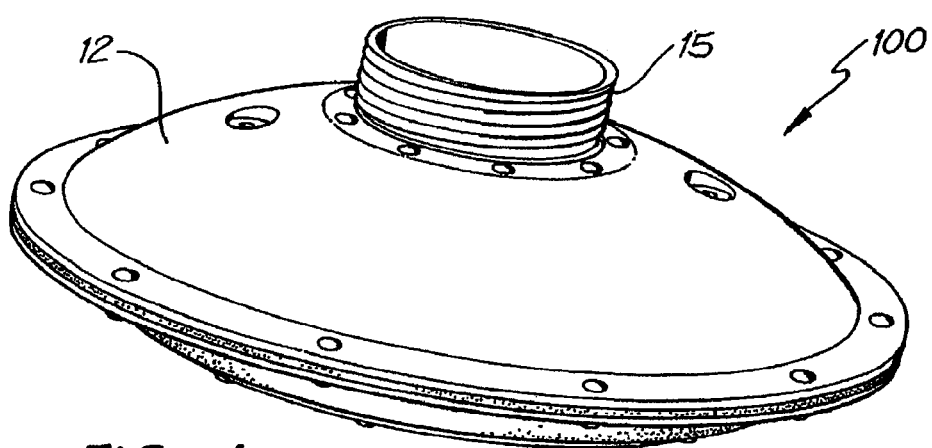
FIG. 4a is a perspective view of a fourth embodiment of a fluid pressure generating means according to the invention.
Figure 4B:
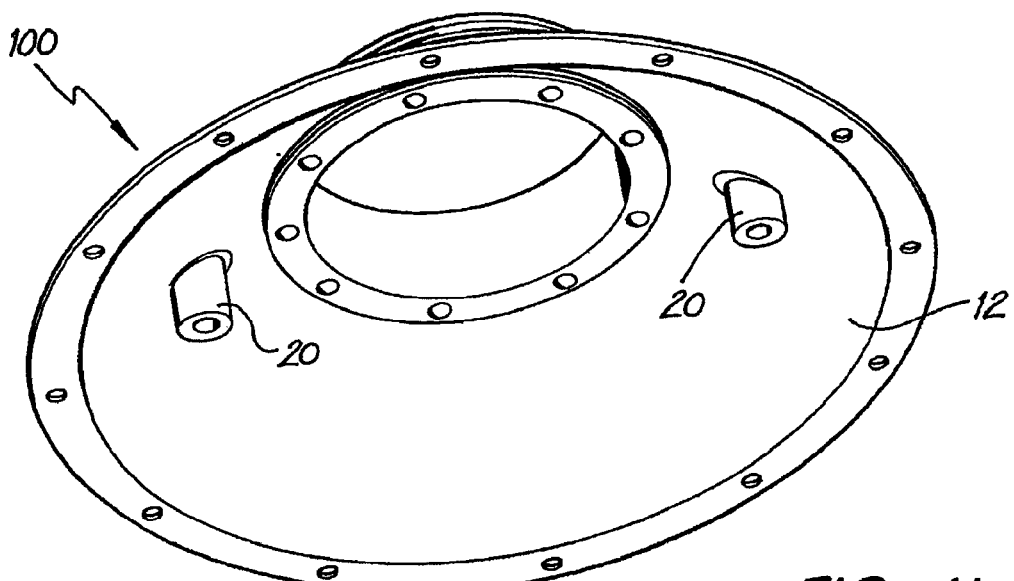
Figure 4C:
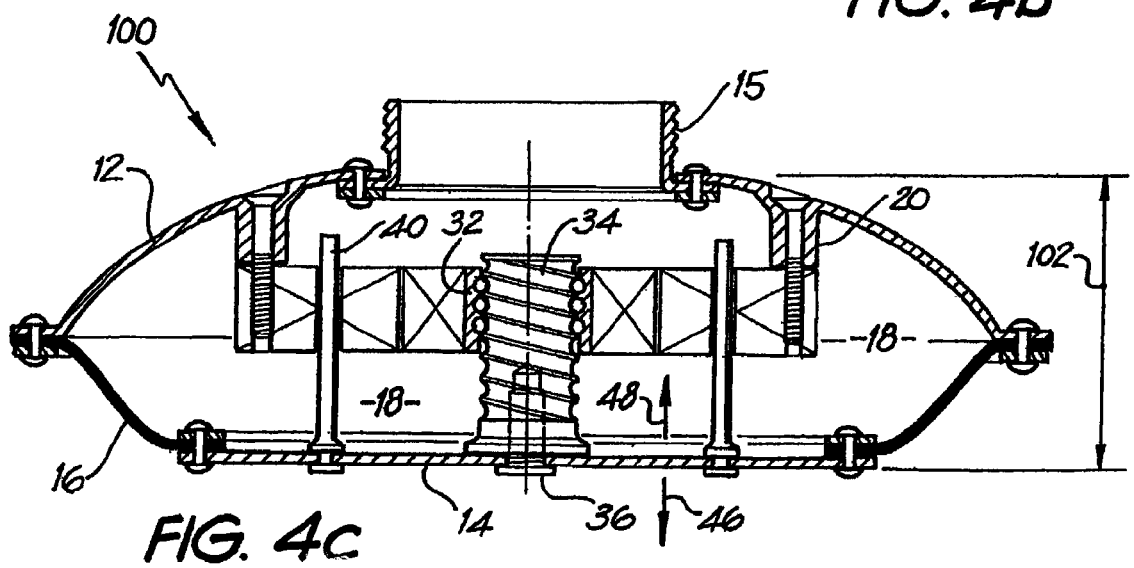

FIGS. 4A to 4C show a fourth embodiment of a fluid pressure generating means according to the invention, in the form of pump 100. The pump 100 is similar to the pump 10 shown in FIG. 1 and like components have been referred to with like reference numerals. However, the pump 100 has been designed to be as thin as possible (dimensions: 82 mm long; 60 mm wide; and 45 mm deep) in order to allow positioning in a patient's chest in contact with the mediastinum adjacent the heart. The pump 100 is placed with the planar housing portion 14 lying in a sagittal plane and with the edge of the housing 100 clear of the inside surface of the chest wall. This orientation is chosen so as to minimize pain and trauma to the patient and also minimize the length of conduit required between the pump 100 and the aortic compression means (not shown). This positioning also assists the surgeon in placing the device.

Figure 5:
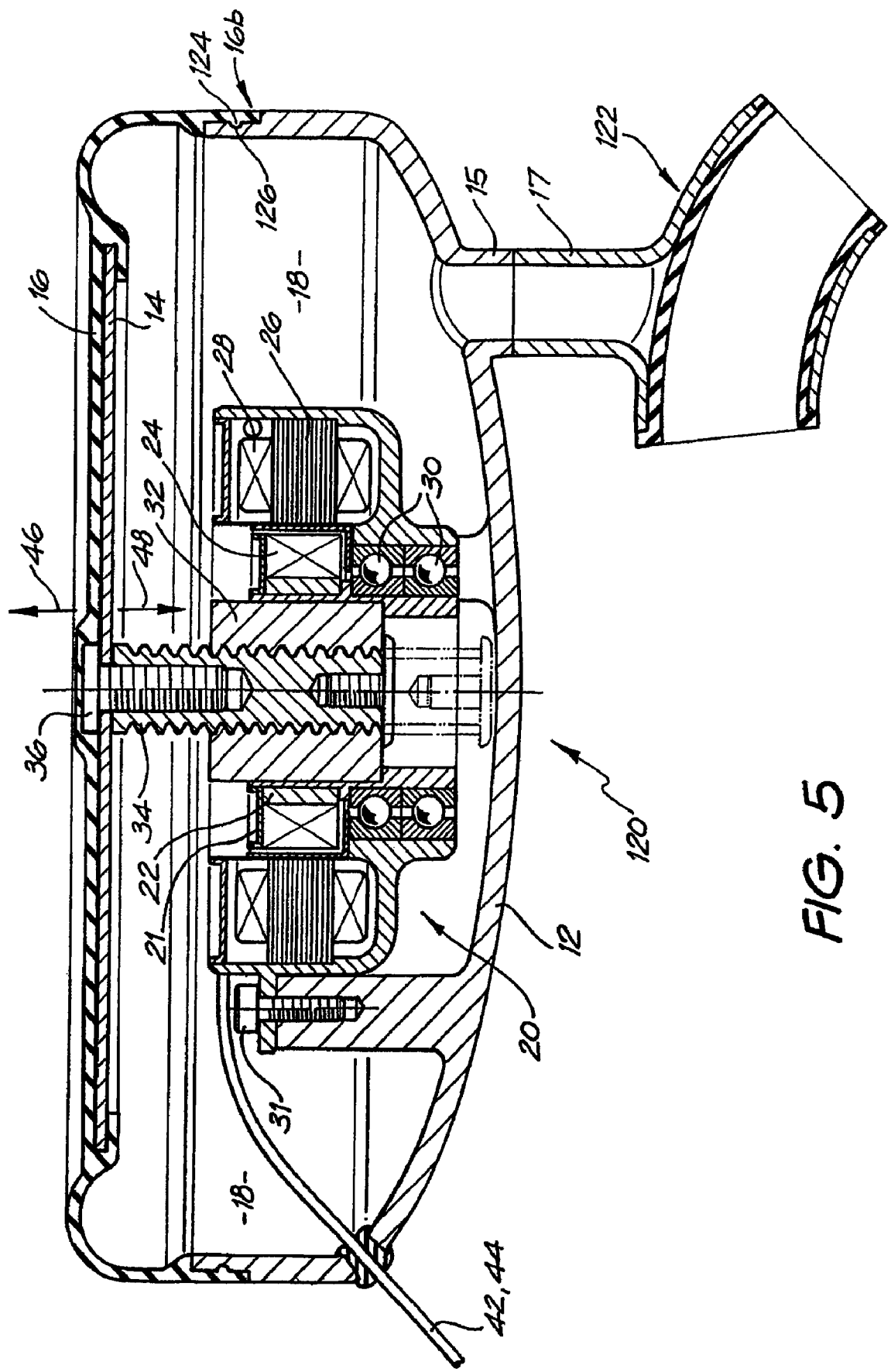
FIG. 5 is a schematic longitudinal sectional view of a fifth embodiment of a heart assist device according to the invention.
Figure 6:
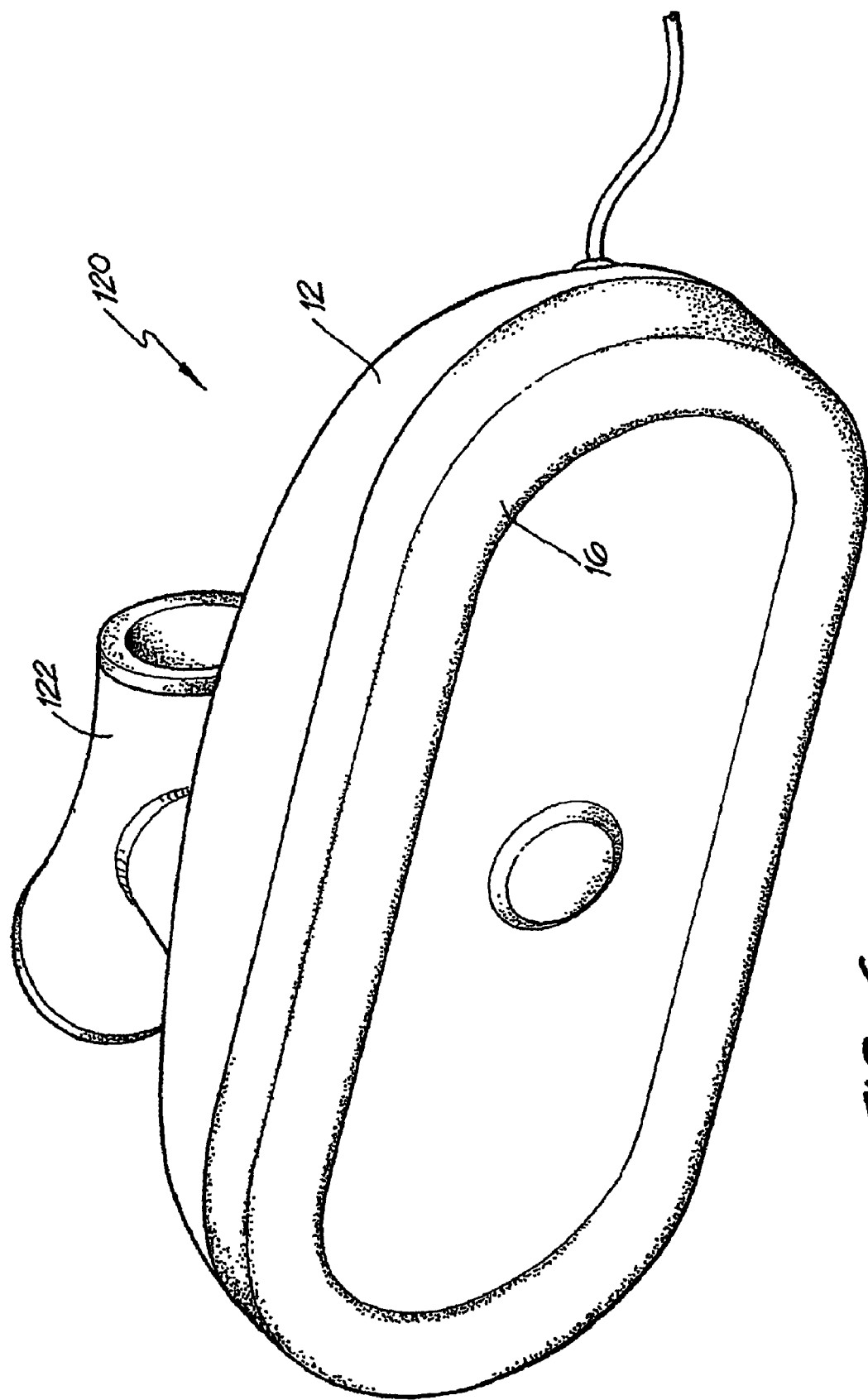
FIG. 6 is a perspective view of the device shown in FIG. 5.
Figure 7:
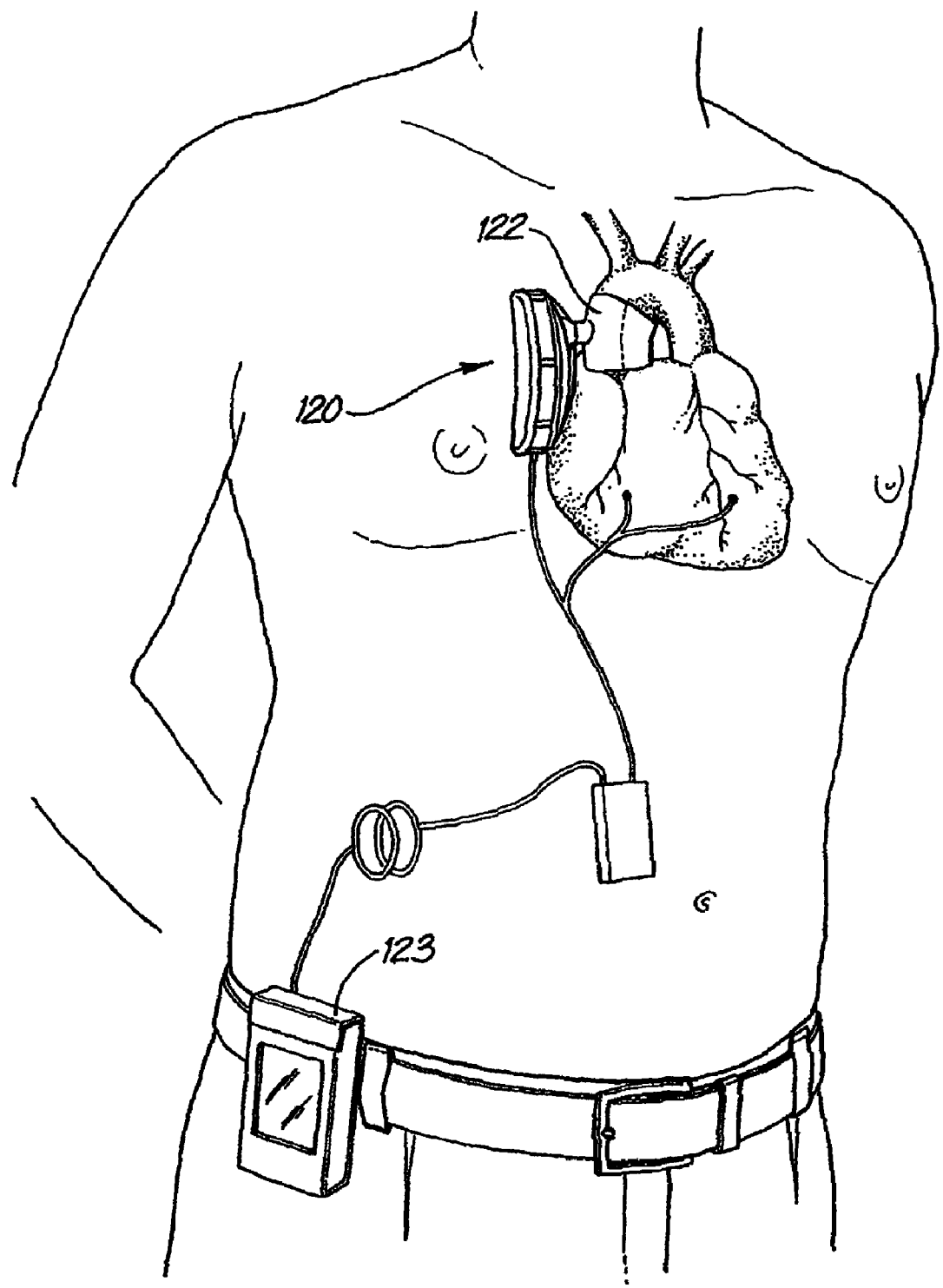
FIG. 7 is a perspective view of the device shown in FIG. 6 after implantation into the pleural cavity, medial to the lung, of a patient.

Referring finally to FIGS. 5 to 7, there is shown a schematic longitudinal sectional view of a fifth embodiment of a fluid pressure generating means according to the invention in the form of pump 120. The pump 120 is shown connected to an aortic compression means or blood pumping means in the form of cuff 122. The construction and operation of the pump 120 is similar to the pump 10 shown in FIG. 1 and like features are indicated with like reference numerals. The size of the pump 120 is similar to the pump 100 shown in FIGS. 4A to 4C, except it is more ovate and has flattened sides (See FIG. 6). The ovate form of the pump 120 and the positioning of the cuff 122 nearer one end allows the device to be placed in the plural cavity, medial to the lung, and lying in a sagittal plane within the patient's body, as is shown in FIG. 7. The pump 120 does not touch the inside surface of the patient's chest wall in this position. FIG. 7 also shows an external battery pack 123 which powers the pump 120.

The main differences between the pumps 10 and 120 are as follows. Firstly, the flexible third housing portion 16 is sealingly connected about its outer edge 16b to the substantially rigid ovate cup-shaped first housing portion 12. The connection and sealing is achieved by a sealing rim 124 on the third portion 16 being snugly received in an annular recess 126 on the first portion 12. Secondly, the substantially rigid flat ovate second housing portion 14 is received within a corresponding recess in the third portion 16, on the interior side of the third portion 16, and is thus within the interior volume 18.

FIG. 5 shows the pump 120 in a position after movement of the second housing portion 14 in the direction 46, which draws fluid into the interior volume 18 from the cuff 122 and deflates same. Driving the threaded shaft 34 in the opposite direction 48 forces the second housing portion 14 towards the motor 20 (see the position of the shaft 34 shown in phantom). As previously described, when this occurs, fluid is forced from the interior volume 18 into the cuff 82 to inflate same.

An advantage of the preferred embodiments of fluid pressure generating means described above is the liquid surrounding the motor is used both as a driving fluid to inflate/deflate the compressions (either directly as per the embodiments of FIGS. 1 and 4 or indirectly as per the embodiment of FIGS. 2 and 3) and as a cooling/lubricating/heat exchanging fluid. The liquid also dampens sound made by the pump mechanism. This simplifies the construction, and minimizes the size, of the fluid pressure generating means.

Whilst the fluid pressure generating means will normally actively drive both the inflation and deflation of the aortic compression means, the motor is preferably designed so that the cogging torque of the motor is sufficiently low that the natural systolic blood pressure of the patient is sufficient to deflate the cuff. If the motor is inactivated for any reason with the cuff in an inflated condition (and thus with the aorta partially occluded), this arrangement means that the natural systolic blood pressure will deflate the cuff by pushing fluid from the cuff into the housing and passively driving the second housing portion away from the motor.

It will be appreciated by person skilled in the art that numerous variations and/or modifications can be made to the invention as shown in the specific embodiments without departing from the spirit or scope of invention as broadly described. For example, the embodiments of the invention are not restricted for use with the embodiments of the heart assist device shown in the PCT application. The specific embodiments are, therefore, to be considered in all respects as illustrative and not restrictive.

The invention claimed is:

1. In a fluid pressure generating device for a heart assist device having a blood pumping means, the improvement comprising:
   a housing defining an interior volume, and having a substantially rigid first housing portion, a substantially rigid second housing portion, a flexible third housing portion extending between the first and second housing portions and an inlet/outlet port connected to one of said housings and adapted to place the interior volume of the housing in fluid communication with the blood pumping means, wherein the third housing has an outer surface about its periphery, an inner surface facing into the interior of the housing and is joined along an edge to the first housing portion;
   a liquid fluid for driving the blood pumping means filling the interior volume of the housing; and
   a motor disposed within the interior volume of the housing and immersed within the fluid for driving the blood pumping means, the motor being connected between the first and second housing portions,
   wherein actuation of the motor moves the first and second housing portions relative to one another to generate fluid pressure changes at the inlet/outlet port, wherein a positive pressure change causes inflation of the blood pumping means and a negative pressure change causes deflation of the blood pumping means.

2. The fluid pressure generating device as claimed in claim 1, wherein the blood pumping means is adapted to displace blood from the aorta of a patient in counter-pulsation with the patient's heart.

3. The fluid pressure generating device as claimed in claim 2, wherein the blood pumping means is adapted to displace blood from the ascending aorta of the patient.

4. The fluid pressure generating device as claimed in claim 1, wherein the fluid pressure generating device is adapted to drive a conventional left ventricular assist device or an extra-ventricular co-pulsation heart compression device.

5. The fluid pressure generating device as claimed in claim 1, wherein one of the first and second housing portions is moveable and the other of the first and second housing portions is fixed, the moveable housing portion being exposed to the outside of the heart assist device and adapted to interface with the lung of a patient.

6. The fluid pressure generating device as claimed in claim 1, wherein one of the first and second housing portions is moveable and the other of the first and second housing portions is fixed, the moveable housing portion not being exposed to the outside of the heart assist device and the device including a flexible compliance chamber.

7. The fluid pressure generating device as claimed in claim 6, wherein the compliance chamber is in contact with the lung of a patient.

8. The fluid pressure generating device as claimed in claim 1, wherein the actuating means includes a nut coupled to one of the first and second housing portions and a threaded shaft coupled to the other of the first and second housing portions, the threaded shaft and the nut being threadedly engaged and the motor being adapted to rotate the nut relative to the threaded shaft.

9. The fluid pressure generating device as claimed in claim 8, wherein the nut is connected to the moveable one of the first and second housing portions and the threaded shaft is connected to the fixed one of the first and second housing portions.

10. The fluid pressure generating device as claimed in claim 7, wherein the threaded shaft is connected to the moveable one of the first and second housing portions and the nut is connected to the fixed one of the first and second housing portions.

11. The fluid pressure generating device as claimed in claim 1, wherein the outflow of the fluid from the inlet/outlet port is axial to the housing.

12. The fluid pressure generating device as claimed in claim 1, wherein the outflow of the fluid from the inlet/outlet port is radial to the housing.

13. The fluid pressure generating device as claimed in claim 1, wherein the outflow of the fluid from the inlet/outlet port is tangential to the housing.

14. The fluid pressure generating device as claimed in claim 1, wherein a surface of the device is curved to fit snugly with the chest wall or mediastinum of a patient.

15. The fluid pressure generating device as claimed in claim 1, wherein the aortic compression means is in the form of a fluid operated cuff adapted to surround the patient's aorta.

16. The fluid pressure generating device as claimed in claim 1, wherein the liquid is an oil or saline.

17. The fluid pressure generating device as claimed in claim 16, wherein the oil is a silicone oil.

18. The fluid pressure generating device as claimed in claim 17, wherein the oil has a viscosity between 10 and 100 centistokes.

19. The fluid pressure generating device as claimed in claim 18, wherein the oil has a viscosity between 10 and 30 centistokes.

* * * * *